(12) United States Patent
Fetzer et al.

(10) Patent No.: US 7,368,117 B2
(45) Date of Patent: May 6, 2008

(54) PRRS VACCINES

(75) Inventors: Christiane Fetzer, Muenster (DE); Stefan Pesch, Muenster (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 88 days.

(21) Appl. No.: 11/275,552

(22) Filed: Jan. 13, 2006

(65) Prior Publication Data

US 2006/0286123 A1 Dec. 21, 2006

(30) Foreign Application Priority Data

Jan. 13, 2005 (EP) .................................. 05000542

(51) Int. Cl.
*A61K 39/12* (2006.01)
(52) U.S. Cl. ........................ 424/204.1; 435/69.1; 435/6
(58) Field of Classification Search ............. 424/204.1; 435/6, 69.1
See application file for complete search history.

(56) References Cited

U.S. PATENT DOCUMENTS

| 5,620,691 | A |   | 4/1997  | Wensvoort et al. |           |
|-----------|---|---|---------|------------------|-----------|
| 5,698,203 | A | * | 12/1997 | Visser et al.    | 424/218.1 |
| 5,925,359 | A | * | 7/1999  | Van Woensel et al. | 424/204.1 |
| 6,197,310 | B1|   | 3/2001  | Wensvoort et al. |           |

FOREIGN PATENT DOCUMENTS

| CA | 2 103 460 C    | 12/1992 |
|----|----------------|---------|
| EP | 0 676 467 A2   | 10/1995 |
| EP | 0 732 340 A2   | 9/1996  |
| EP | 0 835 930 A1   | 4/1998  |
| EP | 1 018 557 A2   | 7/2000  |
| WO | WO 92/21375 A1 | 12/1992 |
| WO | WO 93/03760 A1 | 3/1993  |
| WO | WO 93/06211 A1 | 4/1993  |
| WO | WO 93/07898 A1 | 4/1993  |
| WO | WO 96/36356 A1 | 11/1996 |
| WO | WO 98/18933 A1 | 5/1998  |
| WO | WO 03/062407 A1| 7/2003  |

OTHER PUBLICATIONS

Ying Fang et al; Heterogeneity in Nsp2 of European-Like Porcine Reproductive and respiratory Syndrome Viruses Isolated in the United States; Virus Research (2004) vol. 100 pp. 229-235.
Antoine A.F. De Vries et al; The Genome Organization of the Nidovirales: Similarities and Differences Between Arteri-, Toro-, and Coronaviruses; Seminars in VIROLOGY (1997) vol. 8 pp. 33-47.
H. S. Nielsen et al; Generation of an Infection Clone of VR-2332, a Highly Virulent North American-Type Isolate of Porcine reproductive and Respiratory Syndrome Virus; Journal of Virology (2003) vol. 77 No. 6 pp. 3702-3711.
S. Shen et al; Determination of the Complete Nucleotide Sequence of a Vaccine Strain of Porcine Reproductive and Respiratory Syndrome Virus and Identification of the Nsp2 Gene with a Unique Insertion; Archives of Virology (2000) vol. 145 pp. 871-883.
R. Allende et al; North American and European Porcine Reproductive and Respiratory Syndrome Viruses Differ in Non-Structural Protein Coding Regions; Journal of General Virology (1999) vol. 80 pp. 307-315.
M. B. Oleksiewicz et al; Epitope Mapping Porcine Reproductive and Respiratory Syndrome Virus by Phage Display: the nsp2 Fragment of the Replicase Polyprotein Contains a Cluster of B-Cell Epitopes; Journal of Virology (2001) vol. 75 No. 7 pp. 3277-3290.
Eric J. Snijder et al; Non-Structural Proteins 2 and 3 Interact to Modify Host Cell Membranes During the Formation of the Arterivirus Replication Complex; Journal of General Virology (2001) vol.
M. B. Oleksiewicz et al; Semen from Boars Infected with Porcine Reproductive and respiratory Syndrome Virus (PRRSV) Contains Antibodies Against Structural as Well as Nonstructural Viral Proteins; Veterinary Microbiology (2001) vol. 81 pp. 109-125.
Yvonne Van Der Meer et al; Orf1a-Encoded Replicase Subunits are Involved in the Membrane Association of the Arterivirus Replication Complex; Journal of Virology (1998) vol. 72 No. 8 pp. 6689-6698.
Susan L. Ropp et al; Characterization of Emerging European-Like Porcine Reproductive and Respiratory Syndrome Virus Isolates in the United States; Journal of Virology (2004) vol. 78 No. 7 pp. 3684-3703.
S. Dea et al; Current Knowledge on the Structural Proteins of Porcine Reproductive and Respiratory Syndrome (PRRS) Virus: Comparison of the North American and European Isolates; Archives of Virology (2000) vol. 145 pp. 659-688.
G. Wensvoort et al; Mystery Swine Disease in the Netherlands the Isolation of Lelystad Virus; The Veterinary Quarterly (1991) vol. 13 No. 3 pp. 121-130.
R. Allende et al; Mutations in the Genome of Porcine Reproductive and Respiratory Syndrome Virus Responsible for the Attenuation Phenotype; Archives Virology (2000) vol. 145 pp. 1149-1161.
International Search Report for PCT/EP2006/050098 mailed on Oct. 2, 2007.

* cited by examiner

*Primary Examiner*—Ali R. Salimi
(74) *Attorney, Agent, or Firm*—Michael P. Morris; Mary-Ellen M. Devlin (57) ABSTRACT

The present invention is related to improved modified live PRRS vaccines of European genotype and new PRRSV strains which can be used for the manufacture of such vaccines.

11 Claims, 6 Drawing Sheets

```
                    *        20         *        40         *        60         *        80
Lelystad  : ................................................................................ :
Plaque27  :           ..................................................................... :
Plaque31  :                   ............................................................. :
Plaque36  :                           ..................................................... :
Plaque45  : ..........T..

```
              *        20         *        40         *        60         *        80
P36     : TGAAGGATTGTCCGAGCTCCAAACAGGCCATGGCCCTTCTGGCAAAAATTAAAGTTCCATCCTCAAAGGCCCCGTCTGTGTCCCT
159160  :                   ............................................................................
159178  :                   .....................................................................T...
161009  :                   ............................................................................
169736  :                   ............................................................................
190146  :                   ............................................................................
81984   :                             ..................................................................

*        100        *        120        *        140        *        160        *
P36     : GGACGGGTGTTTCCCTACGGATGTTCCAGCCGACTTCGAGCCAGCATTTCCGGAAAGGCCCCAAAGTTCCGGCGCTGCTGTTGTC
159160  : .............................................C.............------------------------
159178  : .............................................C.............------------------------
161009  : .............................................C.............------------------------
169736  : .............................................C.............------------------------
190146  : .............................................C.............------------------------
81984   : ........................................A...C.............------------------------

180        *        200        *        220        *        240        *
P36     : CTGTGTTCACCGAATGCAAAAGAGTTCGAGGAAACAGCCCCAGAAGAAGTTCAAGAGAGTGGCCACAAGGCCGTCCACTCTGCAC
159160  : ------------------------------------------------------------------------------------
159178  : ------------------------------------------------------------------------------------
161009  : ------------------------------------------------------------------------------------
169736  : ------------------------------------------------------------------------------------
190146  : ------------------------------------------------------------------------------------
81984   : ------------------------------------------------------------------------------------

260        *        280        *        300        *        347        *        340
P36     : TCCTTGCCGAGGGTCCTAACAATGAGCAGGTACAGGTGGTTGCCGGTGAGCAACTGAAGCTCGGCGGTTGTGGTTTGGCAGTCGG
159160  : ------------------------------------------------------------------------------------
159178  : ------------------------------------------------------------------------------------
161009  : ------------------------------------------------------------------------------------
169736  : ------------------------------------------------------------------------------------
190146  : ------------------------------------------------------------------------------------
81984   : ------------------------------------------------------------------------------------

*        360        *        416        *        434        *        420
P36     : GAATGCTCATGAAGGTGTTCCGGTCTCAGCTGGTCTAATTAACCTGGTAGGCGGGAATTTGTCCCCCTCAGACTCCATGAAAGAA
159160  : -------------------------...........................................................
159178  : -------------------------...........................................................
161009  : -------------------------...................................................G.......
169736  : -------------------------...........................................................
190146  : -------------------------...........................................................
81984   : -------------------------...........................................................

*        440        *        460        *        480        *        500        *
P36     : AACATGCTCAATAGCCGGGAAGACGAACCACTGGATTTGTCCCAACCAGCACCAGCTGCCACAACGACCCTTGTGAGAGAGCAAA
159160  : ....................................................................................
159178  : ..................................................T...T............................
161009  : ....................................................................................
169736  : ....................................................................................
190146  : ....................................................................................
81984   : ....................................................................................

520        *
P36     : CACCCGACAACCCAGGTTCTGAT
159160  : ...
159178  : .....
161009  :
169736  : ..
190146  : .......
81984   :
```

Figure 6A

```
                *         20         *         40         *         60         *         80
P36    : TGAAGGATTGTCCGAGCTCCAAACAGGCCATGGCCCTTCTGGCAAAAATTAAAGTTCCATCCTCAAAGGCCCCGTCTGTGTCCCT
115502 : ..........................................................................
159176 :                     ......................................................

*        100         *        120         *        140         *        160         *
P36    : GGACGGGTGTTTCCCTACGGATGTTCCAGCCGACTTCGAGCCAGCATTTCCGGAAAGGCCCCAAAGTTCCGGCGCTGCTGTTGTC
115502 : ............................................C........................-------
159176 : ............................................C........................-------

180         *        200         *        220         *        240         *
P36    : CTGTGTTCACCGAATGCAAAAGAGTTCGAGGAAACAGCCCCAGAAGAAGTTCAAGAGAGTGGCCACAAGGCCGTCCACTCTGCAC
115502 : ------------------------------------------------------------------------
159176 : ------------------------------------------------------------------------

260         *        280         *        300         *        347         *        340
P36    : TCCTTGCCGAGGGTCCTAACAATGAGCAGGTACAGGTGGTTGCCGGTGAGCAACTGAAGCTCGGCGGTTGTGGTTTGGCAGTCGG
115502 : ---------------------------------------..................................
159176 : ---------------------------------------.................t................

*        360         *        416         *        434         *        420
P36    : GAATGCTCATGAAGGTGTTCCGGTCTCAGCTGGTCTAATTAACCTGGTAGGCGGGAATTTGTCCCCCTCAGACTCCATGAAAGAA
115502 : .....T....................................................................
159176 : .....T....................................................................

*        440         *        460         *        480         *        500         *
P36    : AACATGCTCAATAGCCGGGAAGACGAACCACTGGATTTGTCCCAACCAGCACCAGCTGCCACAACGACCCTTGTGAGAGAGCAAA
115502 : .........G................................................................
159176 : .........G.......a........................................................

520         *
P36    : CACCCGACAACCCAGGTTCTGAT : 533
115502 :
159176 :
```

Figure 6B

```
              *         20         *         40         *         60         *         80
P36    : TGAAGGATTGTCCGAGCTCCAAACAGGCCATGGCCCTTCTGGCAAAAATTAAAGTTCCATCCTCAAAGGCCCCGTCTGTGTCCCT
159161 : ..........................................................................
159854 :                      ......................................................

*        100         *        120         *        140         *        160         *
P36    : GGACGGGTGTTTCCCTACGGATGTTCCAGCCGACTTCGAGCCAGCATTTCCGGAAAGGCCCCAAAGTTCCGGCGCTGCTGTTGTC
159161 : ...........................................C.......................................
159854 : ...........................................C.......................................

180         *        200         *        220         *        240         *
P36    : CTGTGTTCACCGAATGCAAAAGAGTTCGAGGAAACAGCCCCAGAAGAAGTTCAAGAGAGTGGCCACAAGGCCGTCCACTCTGCAC
159161 : ............G........................................................................
159854 : ............G........................................................................

260         *        280         *        300         *        347         *        340
P36    : TCCTTGCCGAGGGTCCTAACAATGAGCAGGTACAGGTGGTTGCCGGTGAGCAACTGAAGCTCGGCGGTTGTGGTTTGGCAGTCGG
159161 : ....................T..-----..T...-.------------------------------------------------
159854 : ....................T..-----..G...-.------------------------------------------------

*        360         *        416         *        434         *        420
P36    : GAATGCTCATGAAGGTGTTCCGGTCTCAGCTGGTCTAATTAACCTGGTAGGCGGGAATTTGTCCCCCTCAGACTCCATGAAAGAA
159161 : ------------------------------------------------------------------------------------
159854 : ------------------------------------------------------------------------------------

*        440         *        460         *        480         *        500         *
P36    : AACATGCTCAATAGCCGGGAAGACGAACCACTGGATTTGTCCCAACCAGCACCAGCTGCCACAACGACCCTTGTGAGAGAGCAAA
159161 : -----------.........................................................................
159854 : -----------.........................................................................

520         *
P36    : CACCCGACAACCCAGGTTCTGAT
159161 :
159854 :
```

Figure 6C ns# PRRS VACCINES

BACKGROUND OF THE INVENTION

1. Technical Field

The present invention belongs to the field of vaccines against infectious diseases. More particularly, it relates to vaccines against Porcine Reproductive and Respiratory Syndrome (PRRS), a viral disease affecting pigs.

2. Background Information

The Porcine Reproductive and Respiratory Syndrome Virus (PRRSV) is a (+)stranded ssRNA virus belonging to the family of Arteriviridae. The virus exists as two genotypes referred to as "US" and "EU" type which share about 50% sequence homology (Dea S et al. (2000). Arch Virol 145:659-88), and which can be also distinguished by their immunological properties. Most sequencing information on various isolates is based on the structural proteins, namely the envelope protein GP5 which accounts for only ~4% of the viral genome, while only little is known on the non-structural proteins (nsp).

The nsp2 protein has 1078 amino acids in the EU type prototype Lelystad Virus (LV), and shares only 32% homology with PRRSV-US (Allende R et al. (1999). J Gen Virol 80:307-15). It induces serum antibodies during natural infection (Oleksiewicz M B et al. (2001a). J Virol 75:3277-90, Oleksiewicz M B et al. (2001b). Vet Microbiol 81:109-25), seems to play a crucial role for viral replication (Snijder E J et al. (2001). J Gen Virol 82:985-94, van der Meer Y et al. (1998). J Virol 72:6689-98) and is thought to have species-specific functions (de Vries A A F et al. (1997). Seminars in Virology 8:33-47). The nucleotide sequence coding for the nsp2 amino acid sequence is represented in SEQ ID NO: 2. Length variations in the nsp2 coding region have so far only been described for one US-type isolate (Shen S et al. (2000). Arch Virol 145:871-83) and for EU type strains found in the US (Fang Y et al. Virus Res. 2004 Mar. 15; 100(2):229-35, Ropp S L et al. J Virol. April 2004; 78(7):3684-703.

Isolation of PRRSV and manufacture of vaccines have been described in a number of publications (WO 92/21375, WO 93/06211, WO93/03760, WO 93/07898, WO 96/36356, EP 0 676 467, EP 0 732 340, EP 0 835 930). There is still the need to provide vaccines with improved characteristics, in particular with respect to efficacy and safety.

BRIEF SUMMARY OF THE INVENTION

The present invention is related to improved modified live PRRS vaccines of European genotype and new PRRSV strains which can be used for the manufacture of such vaccines. In particular, the invention provides improved PRRS virus strains that have been deposited with the European Collection of Cell Cultures (ECACC) under the Accession Numbers ECACC 04102703, ECACC 04102702, and ECACC 04102704, or any descendant or progeny of one of the aforementioned strains.

BRIEF DESCRIPTION OF THE DRAWINGS

FIG. 3: Nucleotide sequence of one representative plaque of each length variant compared to the nucleotide sequence of the prototype strain Lelystad Virus (LV).

DETAILED DESCRIPTION OF THE INVENTION

The present invention relates to improved PRRS vaccines. In particular, the invention is related to modified live vaccines (MLV). A modified live vaccine is characterized in that it contains live virus which can replicate in pigs, but does not exert clinical symptoms of PRRS, or only few and moderate symptoms of the disease. Furthermore, upon administration it induces an immunological response in pigs which generally leads to a significant extent of protection against subsequent infection with pathogenic PRRS virus. Virus showing such characteristics is usually called attenuated virus. In general, attenuated virus may be generated form pathogenic virus isolates by repeated passaging in suitable host cells until it shows the desired properties (WO 92/21375, WO 93/06211, WO93/03760, WO 93/07898, WO 96/36356, EP 0 676 467, EP 0 732 340, EP 0 835 930). Alternatively, it may be generated by genetic reengineering through use of an infectious clone, normally a full-length complementary DNA transcript of the viral genome (WO 98/18933, EP 1 018 557, WO 03/062407, Nielsen et al, J Virol 2003, 77:3702-371 1). In a preferred embodiment, the present invention relates to a MLV containing attenuated PRRS virus of European genotype.

The present invention is based on the unexpected finding that safety and efficacy of a PRRS MLV may be improved if it is taken care that the virus used for the vaccine does not show certain deletions in the nsp2 sequence. More specifically, a virus in accordance with the invention should contain a nucleotide sequence of SEQ ID NO: 1, or a nucleotide sequence which differs from SEQ ID NO: 1 by 1, 2, 3, 4, or 5 nucleotides (either substitutions, deletions, or insertions), as part of a full or partial nsp2 coding sequence.

In other words, the nucleotides corresponding to nucleotides Nos. 145 to 163 of SEQ ID NO: 1 should not be deleted in said virus.

Attenuated virus strains which may be used for vaccines in accordance with the present invention have been deposited by Boehringer Ingelheim Vetmedica GmbH according to the Budapest Treaty on 27 Oct. 2004 with the European Collection of Cell Cultures (ECACC), Porton Down, Salisbury, Wiltshire, SP4 0JG, Great Britain, with Accession Numbers 04102703 (PRRSV bs104-P27), 04102702 (PRRSV bs104-P31), and 04102704 (PRRSV bs104-P36). A vaccine according to the present invention should however not contain a virus strain deposited with the ECACC at the same day under the same conditions with Accession Number 04102701 (PRRSV bs104-P45). The deposited strains have been obtained by plaque-purification from a commercially obtainable vaccine product (Porcilis® PRRS, Intervet Deutschland GmbH, Unterschleißheim), as described in the examples. It unexpectedly turned out that said product comprised four sub-clones, with three of these clones (ECACC04102703, ECACC04102702, or ECACC 04102704) having desirable characteristics in accordance with the present invention, making them suitable as ingredients of improved vaccine preparations, while the fourth clone (ECACC04102701) has an undesirable nsp2 deletion.

In one aspect, the present invention is a PPRS virus strain which is any one of the PRRS virus strains that have been deposited on 27 Oct. 2004 with the European Collection of Cell Cultures (ECACC), Porton Down, Salisbury, Wiltshire, SP4 0JG, Great Britain, under the Accession Numbers ECACC 04102703, ECACC 04102702, and ECACC 04102704, or any descendant or progeny of one of the aforementioned strains. The invention therefore extends to PRRS virus strains which are derived from the deposited strains through propagation or multiplication in an identical or divergent form, in particular descendants which possess the essential characteristics of the deposited strains. Upon continued propagation, the strains may acquire mutations most of which will not alter the properties of these strains significantly.

It is clear to the expert that the strains of the invention may be modified to impart further desirable properties to them. This may be achieved by classical propagation and selection techniques, like continued propagation in suitable host cells to extend the attenuated phenotype. This may be furthermore achieved by directed mutation of the nucleic acid sequence of the genome of these strains by suitable genetic engineering techniques. As outlined above, such techniques usually employ construction of a full-length complementary DNA copies (infectious clones) of the viral genome which may then be modified by DNA recombination and manipulation methods (like site-directed mutagenesis etc.). This way, for example antigenic sites or enzymatic properties of viral proteins may be modified. Infectious clones of PRRS virus strains of European and North American genotype have been reported in the literature, see references cited above.

PRRS virus strains suitable for the vaccines of the invention can be grown and harvested by methods known in the art, e.g. by propagating in suitable host cells like the simian cell line MA-104, Vero cells, or porcine alveolar macrophages, as described in the examples. Vaccines comprising any one of PRRSV strains ECACC04102703, ECACC04102702, or ECACC 04102704, as well as any combination of these strains or their descendants, but not PRRSV strain ECACC04102701 are thus preferred embodiments of the present invention. Preferably, vaccines according to the present invention are modified live vaccines comprising one or more of these strains alive in a suitable carrier, but inactivated virus may also be used to prepare killed vaccine (KV). MLV are typically formulated to allow administration of $10^1$ to $10^7$ viral particles per dose, preferably $10^3$ to $10^5$ particles per dose, more preferably $10^4$ to $10^5$ particles per dose (4.0-5.0 $\log_{10}$ $TCID_{50}$). KV may be formulated based on a pre-inactivation titre of $10^3$ to $10^{10}$ viral particles per dose. The vaccine may comprise a pharmaceutically acceptable carrier, for example a physiological salt-solution. The vaccine may or may not comprise an adjuvant. An example of a suitable adjuvant is $\alpha$-tocopherol acetate which can be obtained under the trade name Diluvac Forte®. Alternatively, for example alum based adjuvants may be used.

A vaccine according to the present invention may be presented in form of a freeze-dried preparation of the live virus, to be reconstituted with a solvent, to result in a solution for injection. The solvent may e.g. be water, physiological saline, or buffer, or an adjuvanting solvent. The solvent may contain adjuvants, for example $\alpha$-tocopherol acetate. The reconstituted vaccine may then be injected into the a pig, for example as an intramuscular or intradermal injection into the neck. For intramuscular injection, a volume of 2 ml may be applied, for an intradermal injection it is typically 0.2 ml. In a further aspect, the present invention therefore is a vaccine product, comprising in separate containers a freeze-dried composition of the virus, and a solvent for reconstitution, and optionally further containing a leaflet or label comprising instructions of use.

A vaccine according to the present invention may not only comprise one or more of the aforementioned strains, but may include further components active against PRRS or other porcine viral or bacterial diseases, like porcine circovirus or classical swine fever virus. Therefore, the invention further relates to a vaccine as described, characterised in that it contains at least one further antigen active against a porcine disease which is not PRRS.

EXAMPLES

1. Materials and Methods 1.1. Experimental Infection of Pregnant Sows with Porcilis® PRRS Study Design Fourteen healthy pregnant sows from a confirmed PRRSV negative herd (tested virologically and serologically) were used in this study. Sows faced first or second parturition and were confirmed to be pregnant at the time of vaccination/challenge infection on day 94 (±3) of gestation. They were divided into three treatment groups (table 1). The first group was treated with a commercial dose of Porcilis® PRRS of 2 ml containing at least $10^{4.0} TCID_{50}$ i.m. at day 94 (±3) of gestation. The challenge control group (group 2) received a dose of $10^{4.72}$ $TCID_{50}$ in 2 ml cell culture medium of the pathogenic European field isolate 92045 intranasally. Group 3 was vaccinated with the commercial dose of 2 ml containing $10^{4.0} TCID_{50}$ i.m. Ingelvac PRRS MLV seven days before insemination and was challenged with the European field isolate 92045 ($10^{4.72} TCID_{50}$ in 2 ml cell culture medium i.n.) at day 94 (±3) of gestation.

Animals from group 1 were monitored until day 5 post-farrowing. Animals from group 2 and 3 were monitored until day 28 post farrowing.

Animal Phase

All sows were accustomed to the animal facilities 1 week before vaccination. Sows and piglets were observed for their general health status by the investigator on a daily basis.

Every animal that died or was euthanised was subjected to post-mortem examination and subsequent laboratory analysis.

Pregnancy was confirmed with ultrasound examination. Serum from sows was obtained on study days 0, 7, 14 and at farrowing for PCR and ELISA investigations. Any material that was associated with abortion was subjected to laboratory investigations.

Routine gross pathology was performed on all deadborn piglets. Lung tissue samples from all lung lobes were collected from deadborn piglets and from mummies. Samples for PCR testing were stored at −70° C. 2 ml of precolostral blood from each piglet was collected on the day of birth. Serum was prepared and aliquots were stored at −70° C. Serum was used to test for viremia to evaluate the transplacental infection. All piglets of group 1 that survived until day 5, were euthanized at 5 days of age.

Clinical and Reproductive Performance Parameters

The following main criteria (priority order) were investigated: number of live born piglets per litter, number of stillborn piglets per litter, number of mummified fetuses per litter and number of piglets surviving through day 5 or 28 of age, respectively. The number of piglets born viremic was determined using pre-colostral serum. The frequency of PCR positive blood and tissue samples from sows and/or piglets was investigated to evaluate the epidemiology and course of infection.

1.2 Field Samples

The field samples investigated in this study were taken from routine PRRSV diagnostics and consisted of blood, serum and various organ materials, mostly lungs and lymph nodes, from different European countries. The samples were stored at −20° C. for a maximum of 3 days before RNA preparation and residual material was subsequently transferred to −70° C. for long term storage. RNA and RT-PCR products were stored at −20° C.

1.3. Cell Culturing

Ma104 cells (clone CL2621) were grown in MEM (Dulbecco, Germany) supplemented with 10% FCS and antibiotics.

Porcine alveolar macrophages were harvested using a method described by Wensvoort et al. (Wensvoort, G. et al. Vet. Quat. 1991, 13:121-130) and modified as follows: each lung lobe was infused with 50-100 ml PBS and subsequently massaged for 3 to 5 min. Then the fluid was rescued from the lobe and passed through a gaze filter. This procedure was repeated until the lavage fluid was clear. The pooled lavage fluid was centrifuged at 500 g for 15 min at room temperature. The pellet was washed in PBS and aliquots of $1\times10^7$ cells in 50% RPMI 1640 (Biochrom), 40% FCS and 10% DMSO were frozen at −196° C. For further use the PAMs were cultured in RPMI 1640 medium supplemented with 10% FCS and antibiotics.

1.4. Preparation of Organ Material for Virus Isolation in Cell Culture

About 0.5 $cm^3$ of tissue material was transferred into a tube containing one steel homogenizer ballet in 1.8 ml of sterile PBS. The tubes were agitated for 10 min until the organ material was homogenized. Cell debris was pelleted by centrifugation for 2 min at 450 g and room temperature. The supernatant was passed through a 0.45 μm pore sterile filter and stored at −70° C. Aliquots of 30 μl were used to inoculate one semiconfluent cell culture monolayer using 24 well microtitre plates.

1.5. RNA Isolation

RNA from organ material was extracted with the RNeasy Mini Kit and from serum, plasma, cell culture supernatant and vaccine solution with the QIAamp Viral RNA Mini Kit (both Qiagen) according to the manufacturer's recommendations, using approximately 100 mg organ material and 140 μl fluid material, respectively, for each preparation. The RNA was finally eluted in 65 μl buffer as recommended by the manufacturer.

1.6. Plaque Purification of Virus

Confluent monolayers of Ma104 cells in cell culture dishes of 10 cm Ø seeded 48 hours before were infected with the respective virus at tenfold dilutions from $10^{-1}$ to $10^{-4}$. The cells were incubated for 1 hour with the virus dilutions which were then removed, and the cells were overlaid with 30 ml of Ma104 medium containing 5% methylcellulose (Sigma). Plaques were picked after five to seven days and were transferred to Ma104 monolayers in 24 well plates. Virus from these plates was harvested at about 50% CPE and was subjected to further analysis.

1.7. Immunofluorescence Assay

Cells were fixed at −20° C. for 15 min using ice-cold aceton:methanol (1:1) and air-dried thereafter. After rehydration in PBS, cells were incubated with the PRRSV specific monoclonal antibody SDOW17 (Rural Technologies Inc., USA) diluted 1:1000 in PBS for 1 hour. After 3 washes with PBS, cells were incubated with goat anti-mouse FITC conjugated secondary antibody (Dianova, Hamburg, Germany) (1:150 in PBS) for another hour. After 3 final washes with PBS, cells were overlaid with glycerine:PBS solution (1:1) and subjected to immunofluorescence microscopy.

1.8. Diagnostic nRT-PCR and nsp2 PCR

A diagnostic RT-nPCR was carried out to check the samples for the presence of PRRSV-EU virus; positive samples were then subjected to nsp2 fragment amplification. The primer sequences are listed in table 2.

The diagnostic RT-nPCR was carried out with the Titan One Tube Kit (Roche Molecular Biochemicals) as follows: [5 μl total RNA preparation, 1*RT-PCR buffer, 0.4 mM dNTPs, 20 pmol of primers PLS and PLR, 5 mM dithiothreitol, 1 mM $MgCl_2$, 2.5-5 U RNasin (Promega Ltd), 1-2.5 U enzyme mixture, adjusted to a final volume of 25 μl with DEPC treated aqua dest]. Cycling conditions were as follows: 45° C. for 1 hour, 94° C. for 2 min and 30 cycles of 94° C. for 30 sec, 58° C. for 45 sec and 68° C. for 45 sec, final elongation step at 68° C. for 5 min. The nested PCR reaction was carried out with Qiagen Taq (Qiagen AG) as follows: [1 μl RT-PCR product, 1*PCR buffer, 10 μl Q-solution, 3.5 mM MgCl2, 0.3 mM dNTPs, 20 pmol of each EU-7-n-s and EU-7-n-as primers, 2.5 U Taq polymerase, adjusted to a final volume of 50 μl with aqua dest]. Cycling conditions were as follows: 7 cycles with 94° C. for 1 min, 58° C. for 1 min and 72° C. for 1 min, followed by 30 cycles with 94° C. for 1 min and 70° C. for 1.5 min (no annealing step), final elongation step at 70° C. for 5 min.

Positive samples were then subjected to nsp2 fragment amplification using a one-step reverse transcription PCR with primers EU-1a-2058-s and EU-1a-2683-as with the Qiagen One Step RT-PCR Kit (Qiagen) as follows: [2 μl RNA preparation, 5 μl RT-PCR buffer, 5 μl Q-solution, 0.4 mM dNTPs, 20 pmol of each primer, 2.5-5 U RNasin (Promega), 1 μl One Step enzyme mix, adjusted to a final volume of 25 μl with DEPC treated aqua dest]. Cycling conditions were as follows: 50° C. for 1 hour, 95° C. for 15 min and 40 cycles of 94° C. for 60 sec, 60° C. for 5 sec, 50° C. for 5 sec and 72° C. for 2 min, final elongation step at 72° C. for 10 min.

The nested PCR reaction was carried out with Taq polymerase (Qiagen) and the primer pair EU-1a-2061-s+EU-1a-

2574-as as follows: [1 µl RT-PCR product, 1*PCR buffer, 10 µl Q-solution, 3.5 mM MgCl$_2$, 0.6 mM dNTPs, 20 pmol of each primer, 2.5 U Taq polymerase, adjusted to a final volume of 50 µl with aqua dest]. Cycling conditions were as follows: 8 cycles with 94° C. for 1 min, 60° C. for 5 sec, 50° C. for 5 sec and 68° C. for 45 sec, followed by 50 cycles with 94° C. for 1 min and 70° C. for 1 min (no annealing step), final elongation step at 70° C. for 5 min. The nested PCR primers were elongated with M13 tags to facilitate direct nucleotide sequencing of the PCR products.

1.9. Nucleotide Sequencing

Nucleotide sequencing was performed on the nested PCR products which had been generated with primers that contained an M13 tag, either directly from the PCR reaction or from PCR products that had been excised from agarose gels and purified with the JETsorb gel extraction kit (Genomed). Sequencing was done using the automated sequencer LI-COR DNA Analyzer GENE READIR 4200® (LI-COR Inc., Lincoln, Nebr., USA). Nucleotide and deduced amino acid sequences were analyzed with AlignIR®, vs1.1 (LI-COR Inc., Lincoln, Nebr., USA) and the DNASIS® 2.6 software package (Hitachi Software Genetic Systems Inc., San Francisco, USA).

Figure 1:
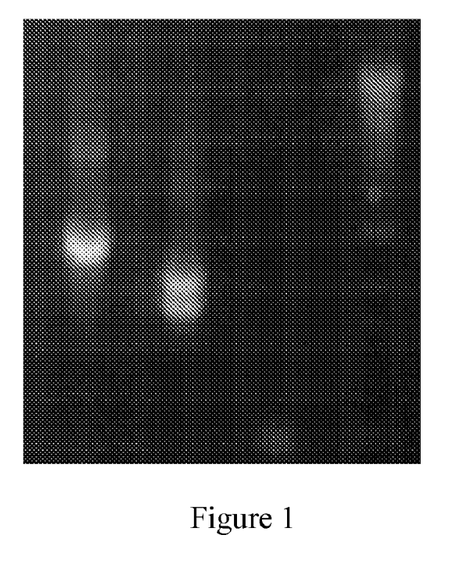
FIG. 1: Agarose gel (2% agarose, ethidium bromide stained) of RT-PCR products obtained from the nsp2 region (pos. 2068-2713) of a Lelystad-like isolate (lane 1), Porcilis® PRRS (lane 2) and negative control (lane 3). Lane 4: 100 bp ladder. The products from Porcilis® PRRS (double band at 434 and 416 bp and band at 347 bp) are smaller than the LV-like product (569 bp).

2. Results 2.1. PCR Analysis of an nsp2 Fragment Generated from the Porcilis® PRRS Vaccine A vial containing 10 doses of freeze-dried Porcilis® PRRS modified live vaccine was reconstituted with 20 ml of sterile PBS. RNA was prepared from this solution and was subjected to amplification of the nsp2 fragment by RT-nPCR as described. RNA from another European Lelystad-like PRRSV strain of known nucleotide sequence was amplified as a positive control in the same experiment. An amplification product of 569 bp was expected for this fragment, and was obtained for the control strain. However, the Porcilis® PRRS sample did not yield such a product. Instead, it showed a double band in a regular 2% agarose gel with one band at about 430 bp and the other at about 350 bp (see FIG. 1).

Both bands were purified separately from the gel and then subjected to nucleotide sequencing. It became obvious that both PCR products had a deletion compared to the nucleotide sequence of Lelystad Virus; however, the sequences obtained were somewhat ambiguous, and the precise scope of the deletion could not be determined. It was therefore decided to plaque-purify the vaccine in order to rule out that the ambiguities were due to a non-homogeneous vaccine strain.

2.2. Characterization of Plaques Obtained from the Porcilis PRRS Vaccine Virus

Again, a vial containing 10 doses of freeze-dried Porcilis® PRRS vaccine was reconstituted with 20 ml of sterile PBS. The reconstituted vaccine solution was incubated with confluent Ma104 monolayers at different dilutions as described in Materials and Methods and then overlaid with methylcellulose containing medium. Plaques were picked after 5 to 7 days of incubation and were grown in 24 well plates on Ma104 until they showed a CPE of about 50%. The cell culture supernatants were then harvested and stored at −70° C.

Figure 2:
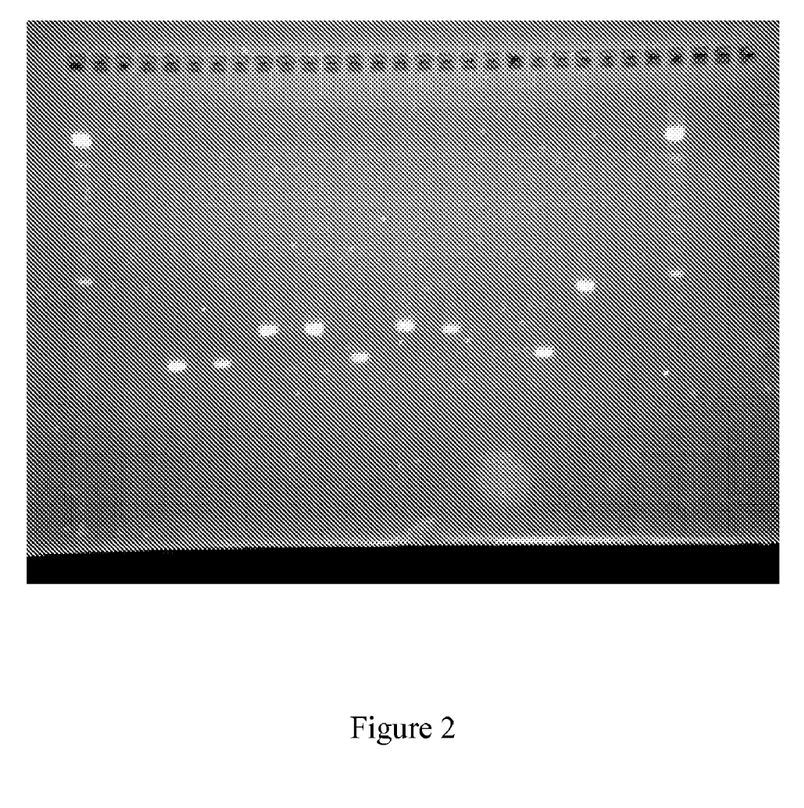
FIG. 2: nsp2 PCR products obtained from a selection of plaques after 1 passage on Ma104 cell culture.

A total of 47 plaques was subjected to further investigation. To this end, RNA was prepared from the supernatants of the first passage on 24 well plates and was used for RT-nPCR amplification of the nsp2 fragment. The resulting PCR products were analyzed on a 2% agarose gel. The result is summarized in table 3. Apart from the mixed populations which were probably due to overlapping plaques, four specific populations were found (in the size range of about 569 bp, 434 bp, 416 bp and 347 bp, respectively). The PCR products of some representative plaques are shown in FIG. 2.

The nucleotide sequence of one representative plaque from each group was then determined by direct sequencing of the nsp2 RT-nPCR products and the following results were obtained: plaque no. 36: no deletion in nsp2; plaque no. 27: deletion of 135 nt; plaque no. 31: deletion of 153 nt; and plaque no. 45: deletion of 222 nt. The nucleotide sequences of these plaques are shown in FIG. 3.

2.3. Experimental Infection of Pregnant Sows with the Porcilis® PRRS Vaccine

Reproductive Parameters

Upon farrowing, sows 7062 and 6677 which had been vaccinated with the Porcilis® PRRS vaccine on day 90 of gestation, showed moderate to severe reproductive failure (see table 4). The proportion of dead and weak born animals was 62.5% in litter 7062 and 44.4% in litter 6677. In addition, until day 5 post farrowing the four live born piglets from sow 7062 and all weak born piglets from the sow 6677 died. The clinical observations are listed in table 5. In conclusion, 5 days after farrowing only 29.4% (5 piglets) of the piglets within both litters still survived.

Six sows from group 2 farrowed after infection with the PRRS field virus isolate 92045. 25.3% and 26.4% of the piglets were born dead or mummified, respectively. Out of 42 piglets born alive, 24 (27.6%) piglets were born weak and only 18 piglets (20.7%) were born normal. Similar to the litters from sows vaccinated with Porcilis® PRRS on day 94 (±3) of gestation, only 29.9% of the piglets born survived.

Sows vaccinated with Ingelvac PRRS® MLV and challenge infected like group 2 farrowed 72.9% normal healthy piglets. 16.7% and 6.2% of the piglets were born dead or mummified, respectively. Although sow 6930 lost all the piglets until day 28 of age, only 2 piglets from other litters died during that period. Thus, 60.4% of the pigs vaccinated with Ingelvac PRRS® MLV and challenge infected with the highly pathogenic PRRS field virus isolate 92045 survived until day 28 of age.

Virological Investigation of Clinical Samples

Sera from sows and piglets as well as lung tissue and body fluid from group 1 piglets were examined for the presence of PRRSV. PCR positive samples were submitted to nucleotide sequencing of the open reading frames 5 and 7 and also of the nsp2 fragment. The results obtained by PCR and virus isolation are listed in table 6.

Figure 4:
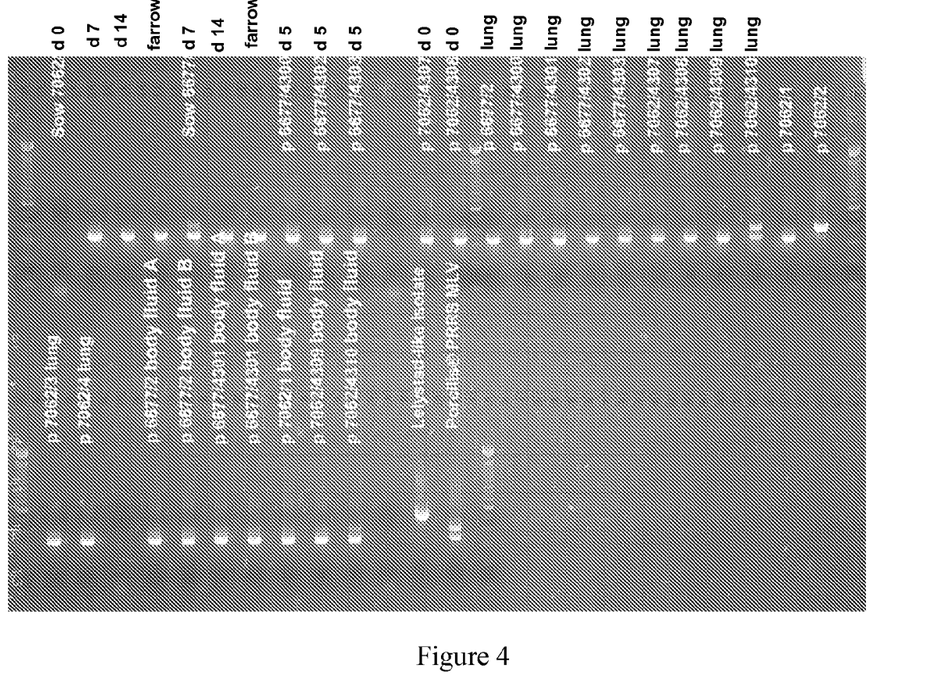
FIG. 4: nsp2 PCR products obtained from different samples of the two sows showing reproductive failure after Porcilis® PRRS vaccination and their offspring.

In the two sows 6677 and 7062 that suffered reproductive failure, every PCR positive sample showed an ORF5 and 7 sequence identical with Porcilis® PRRS, meaning that no other PRRSV strain was detectable in these animals. While PRRSV was found in all dead born piglets from sow 7062, only one dead born piglet from sow 6677 (50%) reacted positive. All weak born piglets from sow 7062 and 67% of weak born piglets as well as 50% of the healthy normal born piglets from sow 6677 yielded positive PCR results which were verified as Porcilis® PRRS by sequence analysis even from samples taken before colostrum uptake. Thus only 4 out of 17 piglets (23.5%) were found to be negative for Porcilis® PRRS. For the nsp2 fragment, every sample showed a strong band at about 347 bp which corresponds to the shortest variant of possible nsp2 fragments that can be amplified from the Porcilis® PRRS vaccine (FIG. 4). Most samples also had a very weak band at about 434 bp; only piglet 7062/4310 had a strong double band.

For differential diagnosis, organ material as well serum were investigated for the US genotype of PRRSV and for PPV, BVD, CSFV, BDV, PrV, PCV2, SIV, PEV/PTV, swPara-myxoV, EMCV, swHEV as well as on *Leptospira* spp., *Chlamydophila* spp. And *Chlamydia* spp. All these investigations yielded negative results.

Virus Isolation on Ma104 and on Porcine Alveolar Macrophages

Lung material from five piglets of each sow was subjected to virus isolation attempts on Ma104 cells and on porcine alveolar macrophages, choosing two dead born and three live born piglets from each sow (see table 6). An aliquot of 30 μl of homogenized and sterile filtered organ suspension was used for inoculation of one well of Ma104 cells and PAM cells, respectively. Cells were incubated at 37° C. and 5% $CO_2$ for 5 days and then stained in an immunofluorescence assay with the PRRSV specific monoclonal antibody SDOW17. Out of the ten organ suspensions, four yielded a cythopathic effect and positive staining results on both Ma104 and PAM cells. The remaining six samples yielded negative results on both cell types.

From each positive sample, RNA was prepared from the respective cell culture supernatants from both PAM and Ma104 cells. RNA was subjected to RT-nPCR for the ORF 5 and 7 as well as for the nsp2 fragment. Nucleotide sequencing of the ORF 5 and 7 PCR products confirmed the virus as Porcilis® PRRS. The nsp2 PCR product unambiguously yielded the Porcilis® PRRS sequence with the largest deletion of 222 nucleotides.

Resulting out of these experiments, it can be concluded that the variant represented by plaque 45 and deposited under ECACC04102701 is preferably responsible for transplacental infection and the reproductive performance reduction observed.

Figure 5:
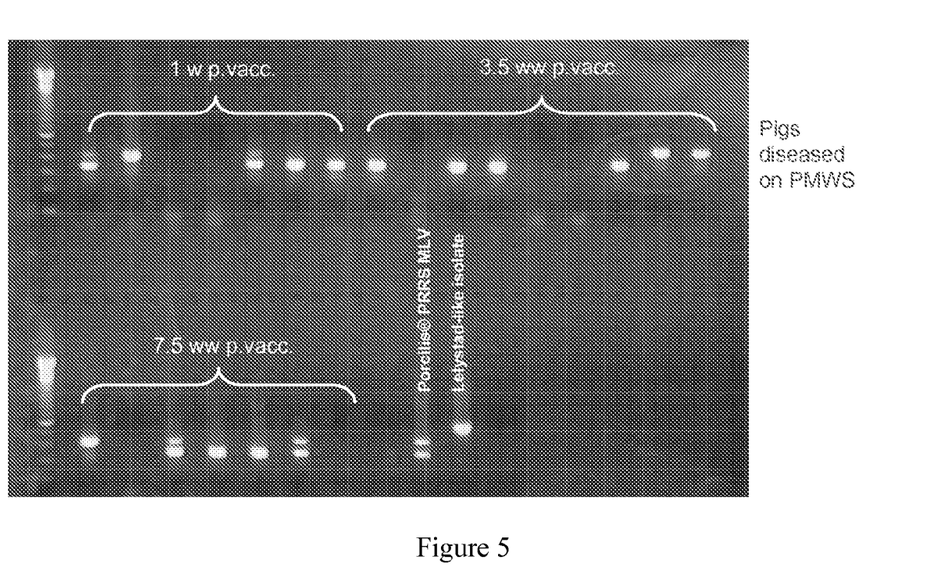
FIG. 5: nsp2 PCR products obtained from clinical samples of piglets vaccinated with Porcilis® PRRS at 6 weeks of age. Circle shows samples of pigs diseased on PMWS.

2.4. Analysis of the nsp2 Amplification Product Obtained from Field Samples of Pigs Previously Vaccinated with the Porcilis® PRRS Vaccine a) Samples from a Farm Vaccinated with Porcilis PRRS A PRRSV field virus negative herd that regularly vaccinated the piglets with Porcilis® PRRS at the age of 6 weeks was investigated for PRRSV-EU. Ten samples each were taken from piglets aged 4, 7, 9.5 and 13.5 weeks, respectively. In the 9.5 weeks group, three piglets were suffering from the Postweaning Multisystemic Wasting Syndrome (PMWS), which is often correlated with porcine circovirus 2 and PRRS coinfection (Ellis et al, Vet Microbiol 2004, 98:159-163). A PRRSV-EU specific RT-nPCR product was obtained for ⅒, ⁷⁄₁₀, ⁹⁄₁₀ and ⁷⁄₁₀ animals before vaccination, at 1, 3.5 and 7.5 weeks after vaccination. Upon RT-PCR amplification of the nsp2 coding region from the PRRSV positive samples, only Porcilis® PRRS typical PCR products were obtained: 8 samples yielded only the ~347 bp product, 4 samples only the ~434 bp product and 4 samples the double band of 434 and 347 bp. No sample gave the Lelystad-like product (see FIG. 5). The nsp2 region could be amplified in three of the four PMWS diseased piglets, two of which showed the 434 bp product and one the 347 bp product.

b) Nsp2 Length Variation in Field Samples from Routine Diagnostics

Figure 6A:
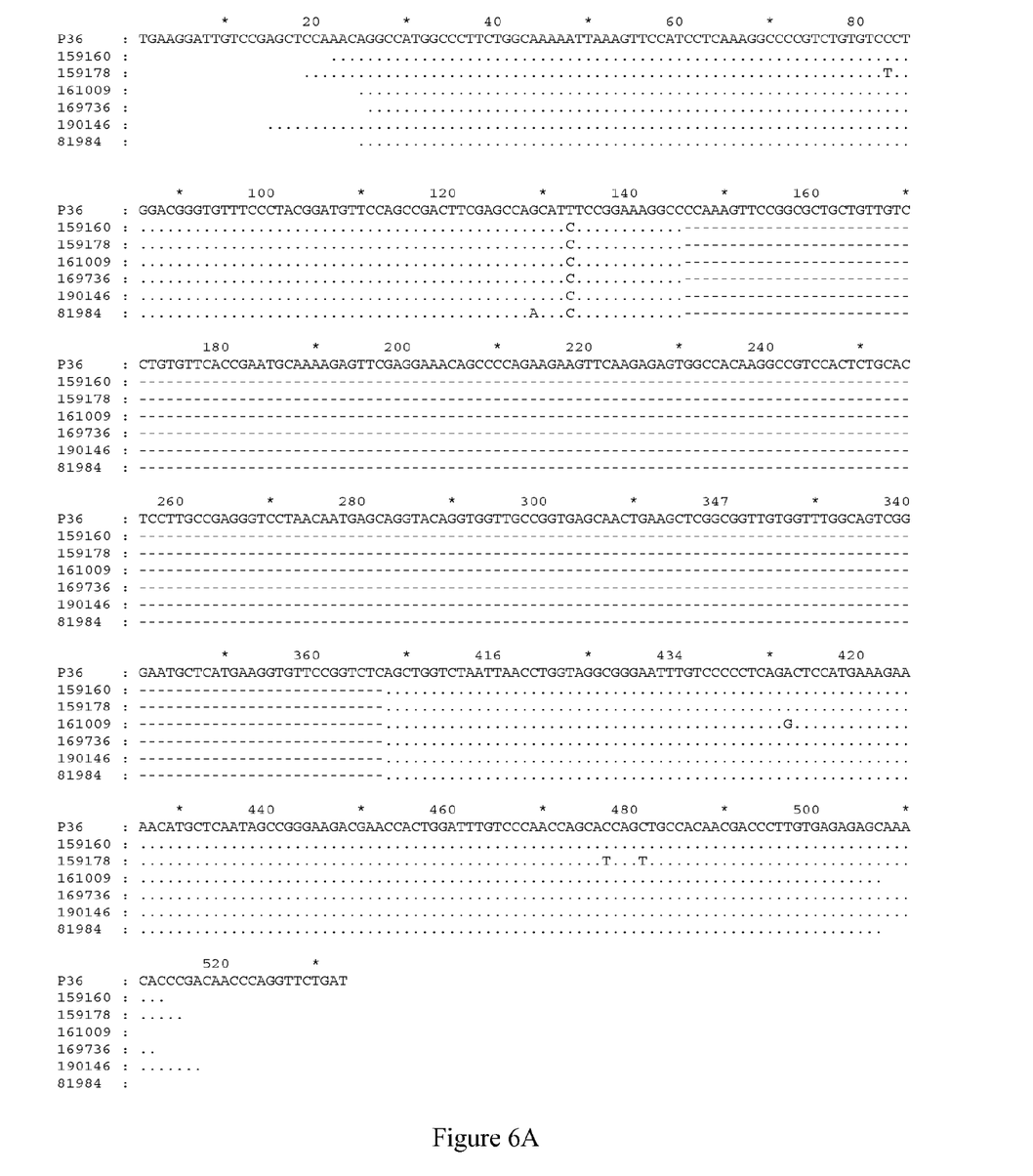
FIG. 6A: Nucleotide sequence of nsp2 PCR products obtained from different field samples showing the same deletion of 222 nucleotides as one group of plaques derived from the Porcilis PRRS vaccine bottle (e.g. plaque P45), compared to the full-length (Lelystad-like) sequence of the Porcilis-derived plaque 36.
Figure 6B:
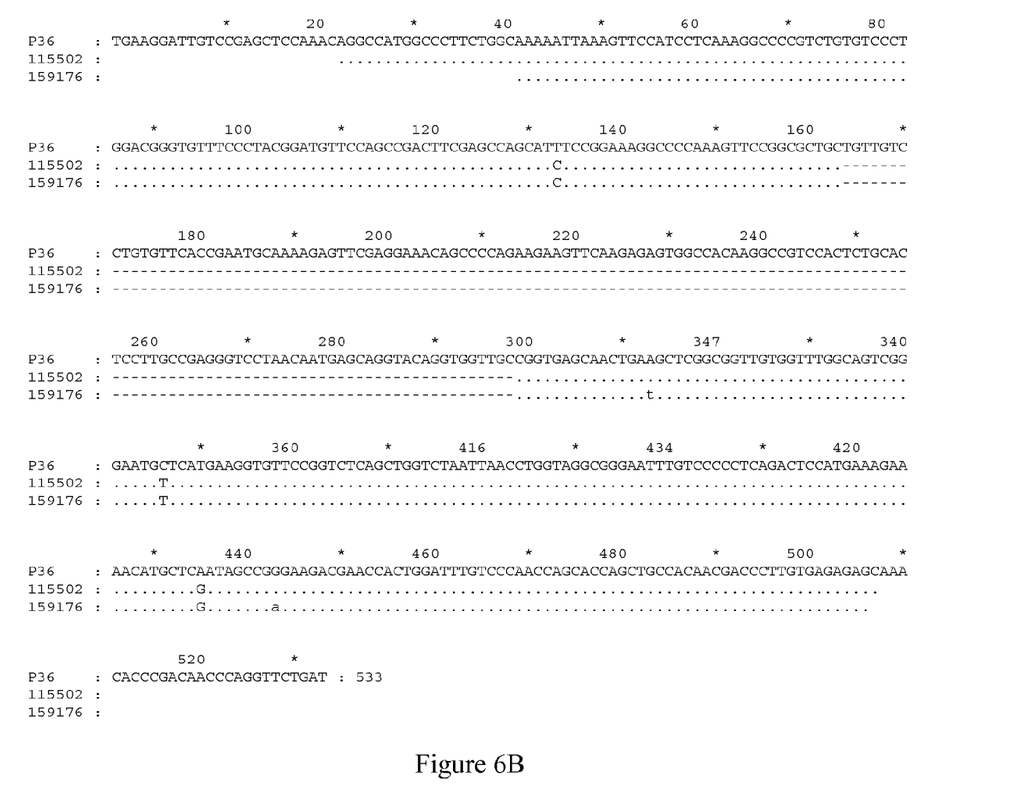
FIG. 6B: Nucleotide sequence of nsp2 PCR products obtained from different field samples showing the same deletion of 135 nucleotides as one group of plaques derived from the Porcilis PRRS vaccine bottle (e.g. plaque P27), compared to the full-length (Lelystad-like) sequence of the Porcilis-derived plaque 36
Figure 6C:
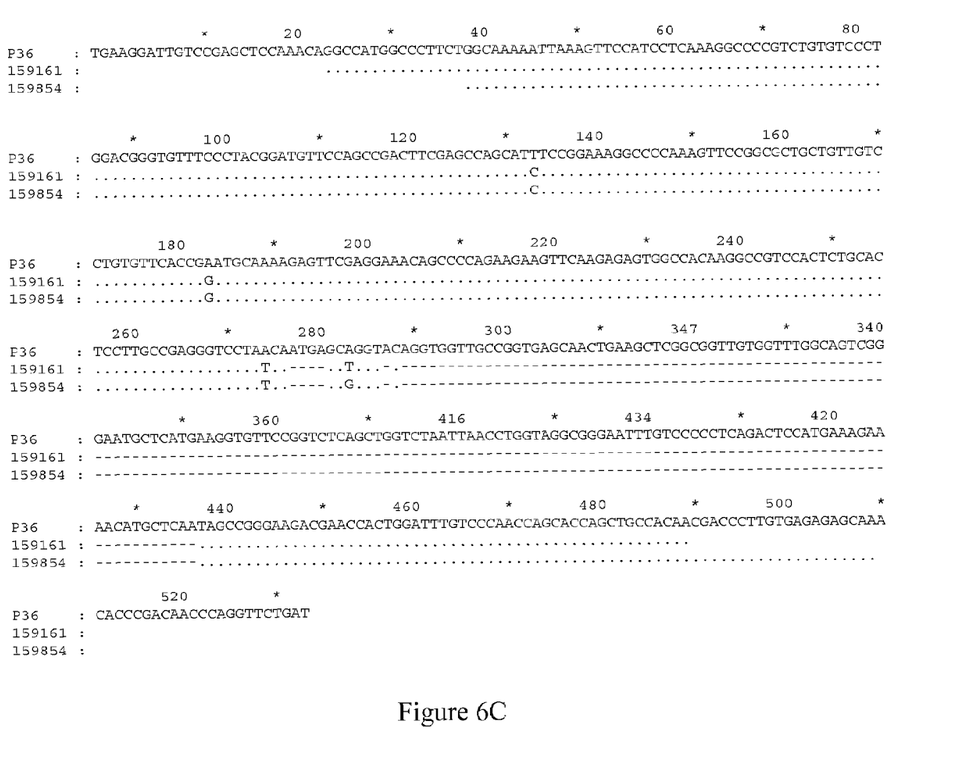
FIG. 6C: Nucleotide sequence of nsp2 PCR products obtained from different field samples showing the same deletion of 153 nucleotides as one group of plaques derived from the Porcilis PRRS vaccine bottle (e.g. plaque 31), compared to the full-length (Lelystad-like) sequence of the Porcilis-derived plaque 36

A total of 514 blood and tissue samples which had been sent in for diagnostics from PRRS suspected herds and had been PRRSV positive in routine RT-nPCR was subjected to nsp2 fragment amplification. Amplification products were obtained in 41.4% out of 514 samples. Deletions of varying length were found in 30.7% of the analyzed samples, which indicates a total frequency of at least 12.7% nsp 2 deletion variants in the field. In most cases, the bands found showed the same pattern as found with the Porcilis® PRRS vaccine, consisting of a (double) band of 434 and 416 bp which cannot easily be differentiated on a regular 2% agarose gel, or a band of 347 bp. A selection of samples was therefore subjected to nucleotide sequencing to check whether these PCR products were in fact derived from Porcilis® PRRS vaccine virus. The results are shown in FIG. 6A-C.

TABLE 1

Study groups and treatment

| Group | Sows n | Vaccination seven days before insemination | Vaccination/ Infection at day 94 (+/−3) of gestation | Dose |
|---|---|---|---|---|
| 1 | 2 | — | Porcilis ® PRRS | >$10^{4.0}$ $TCID_{50}$ in 2 ml i.m. |
| 2 | 6 | — | European field isolate 92045 passage 3 | $10^{4.72}$ $TCID_{50}$ in 2 ml i.n. |
| 3 | 6 | Ingelvac ® PRRS MLV | European field isolate 92045 passage 3 | $10^{4.72}$ $TCID_{50}$ in 2 ml i.m. | n—number of sows;
i.m. intramuscularly,
i.n. intranasally

TABLE 2

Primer sequences for generating nsp2 RT-PCR products

| Name | Sequence | Purpose |
|---|---|---|
| PLS | ATGGCCAGCCAGTCAATC | RT-PCR ORF7 |
| PLR | TCGCCCTAATTGAATAGGTG | RT-PCR ORF7 |
| EU-7-n-s | TGTAAAACGACGGCCAGT*ATGATAAAGTCCCAGC GCCAG* | nPCR ORF7 |
| EU-7-n-as | CAGGAAACAGCTATGACC*CTGTATGAGCAACCGG CAGCAT* | nPCR ORF7 |
| EU-1a-2058-s | TGTTGAAGGATTGTCCGAGCTCC | RT-PCR ORF1a |
| EU-1a-2683-as | AGATCCAAAGGCGAACTGCTG | RT-PCR ORF1a |
| EU-1a-2061-s | TGTAAAACGACGGCCAGT*TGAAGGATTGTCCGAG CTCC* | nPCR ORF1a |
| EU-1a-2574-as | CAGGAAACAGCTATGACC*ATCAGAACCTGGGTTG TCGG* | nPCR ORF1a |

For the nested PCR primers, M13 tags are marked *italic*, while the PRRSV specific sequence of the primers is underlined.

TABLE 3 nsp2 PCR results from 47 plaques after 1 passage in Ma104 cell culture

| PCR product length | Σ plaques | Plaque no. |
|---|---|---|
| ~569 bp | 2 | 36, 58 |
| ~434 bp | 10 | 24, 27, 32, 43, 46, 49, 53, 55, 57, 59 |
| ~416 bp | 1 | 31 |
| ~347 bp | 20 | 8, 9, 10, 11, 12, 13, 25, 26, 28, 33, 37, 38, 40, 42, 44, 45, 47, 51, 54, 56 |
| Mixed | 14 | 1, 2, 4, 5, 6, 7, 15, 16, 18, 30, 34, 35, 41, 48, 19, 50, 52 |

TABLE 4

Comparison of the reproductive and production parameters of sows vaccinated with Porcilis ® PRRS at day 94 (+/−) with challenge and vaccinated/challenge controls

| Group | Sow ID | n | Piglets born alive Total | Normal | Weak | Piglets born Dead/Mummified | Piglets died until 5/28 DoA | Total piglets alive at 5/28 DoA |
|---|---|---|---|---|---|---|---|---|
| 1 | 7062 | 8 | 4 | 3 | 1 | 4/0 | 4 | 0 |
|   | 6677 | 9 | 7 | 5 | 2 | 2/0 | 2 | 5 |
|   | mean | 8.5 | 5.5 | 4.0 | 1.5 | 3.0 | 3.0 | 2.5 |
|   | total | 17 | 11 | 8 | 3 | 6/0 | 6 | 5 |
|   | % |   | 64.7 | 47.0 | 17.7 | 35.3/0 | 35.3 | 29.4 |
| 2 | 6746 | 16 | 13 | 2 | 11 | 3/0 | 7 | 6 |
|   | 7008 | 13 | 8 | 5 | 3 | 3/2 | 2 | 6 |
|   | 7076 | 15 | 7 | 2 | 5 | 4/4 | 2 | 5 |
|   | 7086 | 13 | 9 | 8 | 1 | 4/0 | 3 | 6 |
|   | 7091 | 15 | 3 | 1 | 2 | 4/8 | 1 | 2 |
|   | 7145 | 15 | 2 | 0 | 2 | 4/9 | 1 | 1 |
|   | Mean | 14.5 | 7.0 | 3.0 | 4.0 | 3.7/3.8 | 2.7 | 4.3 |
|   | Total | 87 | 42 | 18 | 24 | 22/23 | 16 | 26 |
|   | % |   | 48.3 | 20.7 | 27.6 | 25.3/26.4 | 38.1 | 29.9 |
| 3 | 6678 | 11 | 10 | 9 | 1 | 1/0 | 1 | 9 |
|   | 6930 | 7 | 6 | 5 | 1 | 1/0 | 6 | 0 |
|   | 6955 | 6 | 3 | 3 | 0 | 3/0 | 0 | 3 |
|   | 7095 | 9 | 6 | 6 | 0 | 2/1 | 1 | 5 |
|   | 7158 | 15 | 12 | 12 | 0 | 1/2 | 0 | 12 |
|   | Mean | 9.6 | 7.4 | 7.0 | 0.4 | 1.6/0.8 | 1.6 | 5.8 |
|   | Total | 48 | 37 | 35 | 2 | 8/3 | 8 | 29 |
|   | % |   | 77.1 | 72.9 | 4.2 | 16.7/6.2 | 21.6 | 60.4 |

TABLE 5

Clinical assessment of the offspring of the sows vaccinated with Porcilis ® PRRS on day 90 of gestation (group 1)

| Sow ID | Pig ID | Day of age 0 | 1 | 2 | 3 | 4 | 5 |
|---|---|---|---|---|---|---|---|
| 6677 | 4300 | — | — | W | W | W | W |
|   | 4301 | — | W, Dep | Died |   |   |   |
|   | 4302 | — | — | W | W | W | — |
|   | 4303 | — | — | — | — | — | — |
|   | 4304 | W | Died |   |   |   |   |
|   | 4305 | — | Died[1] |   |   |   |   |
|   | 4306 | W | — | W, A | W, A | W, Dep | W, A |
|   | 1 | Born dead |   |   |   |   |   |
|   | 2 | Born dead |   |   |   |   |   |
| 7062 | 4307 | — | W, Dep | W, Dep | W, Dep | Died[2] |   |
|   | 4308 | W | Died[2] |   |   |   |   |
|   | 4309 | — | W, Dep | Died |   |   |   |
|   | 4310 | — | — | W, Dep | Died[3] |   |   |
|   | 1 | Born dead |   |   |   |   |   |
|   | 2 | Born dead |   |   |   |   |   |
|   | 3 | Born dead |   |   |   |   |   |
|   | 4 | Born dead |   |   |   |   |   |

W = weak,
Dep = depressed,
A = anorexia
[1]Piglet 4305 died on day 1 due to a blood taking accident.
[2]Piglets 4307 and 4308 died due to agalactia.
[3]Piglet 4310 showed severe signs of pneumonia.

TABLE 6

Virological results from sows vaccinated with Porcilis ® PRRS at day 94 (+/−3) of gestation and their litters

| Sow/Piglet ID | Material | PRRSV-EU (PCR) | Porcilis PRRS verified by sequencing* | Reisolates of Porcilis PRRS MLV on PAMs** | Reisolates of Porcilis PRRS MLV on Ma104** |
|---|---|---|---|---|---|
| 6677 | serum, day 0 | neg | nd. | nd. | nd. |
|   | serum, day 7 | pos | yes | nd. | nd. |
|   | serum, day 14 | pos | yes | nd. | nd. |
|   | serum, day of farrowing | pos | yes | nd. | nd. |

TABLE 6-continued

Virological results from sows vaccinated with Porcilis ® PRRS at day 94 (+/−3) of gestation and their litters

| Sow/Piglet ID | Material | PRRSV-EU (PCR) | Porcilis PRRS verified by sequencing* | Reisolates of Porcilis PRRS MLV on PAMs** | Reisolates of Porcilis PRRS MLV on Ma104** |
|---|---|---|---|---|---|
| 7062 | serum, day 0 | neg | nd. | nd. | nd. |
|  | serum, day 7 | pos | yes | nd. | nd. |
|  | serum, day 14 | pos | yes | nd. | nd. |
|  | serum, day of farrowing | pos | yes | nd. | nd. |
| 6677/1 | lung tissue | neg | nd. | neg | neg |
| 6677/2 | lung tissue | pos | yes | neg | neg |
| 6677/4300 | lung tissue | pos | yes | nd. | nd. |
| 6677/4301 | lung tissue | pos | yes | pos | pos |
| 6677/4302 | lung tissue | pos | yes | neg | neg |
| 6677/4303 | lung tissue | pos | yes | pos | pos |
| 6677/4304 | lung tissue | neg | nd. | nd. | nd. |
| 6677/4305 | lung tissue | neg | nd. | nd. | nd. |
| 6677/4306 | lung tissue | neg | nd. | nd. | nd. |
| 7062/1 | lung tissue | pos | yes | neg | neg |
| 7062/2 | lung tissue | pos | yes | neg | neg |
| 7062/3 | lung tissue | pos | yes | nd. | nd. |
| 7062/4 | lung tissue | pos | yes | nd. | nd. |
| 7062/4307 | lung tissue | pos | yes | pos | pos |
| 7062/4308 | lung tissue | pos | yes | pos | pos |
| 7062/4309 | lung tissue | pos | yes | neg | neg. |
| 7062/4310 | lung tissue | pos | yes | nd. | nd. | nd: not done
*The PCR fragment of the routinely performed diagnostic PCR was sequenced
**All reisolates obtained from MA 104 and PAMs were sequenced in ORF5 and ORF 7 and were identical with Porcilis ® PRRS

TABLE 7

History of samples showing an nsp2 deletion PCR product; cf. FIG. 6A

| Sample ID | Origin | | History |
|---|---|---|---|
| 115502 | Hungary | 2004 33 d.p.i. | animal vaccinated with Porcilis ® PRRS in a controlled study experiment |
| 159160 | Great Britain | 2003 non-vaccinated piglet, 4 weeks old, in a herd that is regularly vaccinated with Porcilis ® PRRS | healthy piglet |
| 159178 | Great Britain | 2003 piglet vaccinated with Porcilis ® PRRS at the age of 6 weeks, 24 days post vaccination | piglet is showing respiratory disease |

TABLE 8

History of samples showing an nsp2 deletion PCR product; cf. FIG. 6B

| Sample ID | Origin | | History |
|---|---|---|---|
| 115502 | Hungary | 2004 33 d.p.i. | animal vaccinated with Porcilis ® PRRS in a controlled study experiment |
| 159176 | Great Britain | 2003 piglet vaccinated with Porcilis ® PRRS at the age of 6 weeks, 24 days post vaccination | piglet is showing respiratory disease |

TABLE 9

History of samples showing an nsp2 deletion PCR product; cf. FIG. 6C

| Sample ID | Origin | | History |
|---|---|---|---|
| 159161 | Great Britain | 2003 piglet vaccinated with Porcilis ® PRRS at the age of 6 weeks, 7 days post vaccination | healthy piglet |

SEQUENCE LISTING

<160> NUMBER OF SEQ ID NOS: 11

<210> SEQ ID NO 1
<211> LENGTH: 18
<212> TYPE: DNA
<213> ORGANISM: Porcine reproductive and respiratory syndrome virus

<400> SEQUENCE: 1
ccaaagttcc ggcgctgc                                                    18

<210> SEQ ID NO 2
<211> LENGTH: 533
<212> TYPE: DNA
<213> ORGANISM: Porcine reproductive and respiratory syndrome virus

<400> SEQUENCE: 2
tgaaggattg tccgagctcc aaacaggcca tggcccttct ggcaaaaatt aaagttccat      60
cctcaaaggc cccgtctgtg tccctggacg ggtgtttccc tacggatgtt ccagccgact    120
tcgagccagc atctccggaa aggccccaaa gttccggcgc tgctgttgtc ctgtgttcac    180
cggatgcaaa agagttcgag gaaacagccc cagaagaagt tcaagagagt ggccacaagg    240
ccgtccactc tgcactcctt gccgagggtc ctaacaatga gcaggtacag gtggttgccg    300
gtgagcaact gaagctcggc ggttgtggtt tggcagtcgg gaatgctcat gaaggtgttc    360
cggtctcagc tggtctaatt aacctggtag gcgggaattt gtccccctca gactccatga    420
aagaaaacat gctcaatagc cgggaagacg aaccactgga tttgtcccaa ccagcaccag    480
ctgccacaac gaccccttgtg agagagcaaa caccccgacaa cccaggttct gat          533

<210> SEQ ID NO 3
<211> LENGTH: 533
<212> TYPE: DNA
<213> ORGANISM: Porcine reproductive and respiratory syndrome virus

<400> SEQUENCE: 3
tgaaggattg tccgagctcc aaacaggcca tggcccttct ggcaaaaatt aaagttccat      60
cctcaaaggc cccgtctgtg tccctggacg ggtgtttccc tacggatgtt ccagccgact    120
tcgagccagc atttccggaa aggccccaaa gttccggcgc tgctgttgtc ctgtgttcac    180
cgaatgcaaa agagttcgag gaaacagccc cagaagaagt tcaagagagt ggccacaagg    240
ccgtccactc tgcactcctt gccgagggtc ctaacaatga gcaggtacag gtggttgccg    300
gtgagcaact gaagctcggc ggttgtggtt tggcagtcgg gaatgctcat gaaggtgttc    360
cggtctcagc tggtctaatt aacctggtag gcgggaattt gtccccctca gactccatga    420
aagaaaacat gctcaatagc cgggaagacg aaccactgga tttgtcccaa ccagcaccag    480
ctgccacaac gaccccttgtg agagagcaaa caccccgacaa cccaggttct gat          533

<210> SEQ ID NO 4
<211> LENGTH: 18
<212> TYPE: DNA
<213> ORGANISM: Artificial
<220> FEATURE:
<223> OTHER INFORMATION: dna reverse transcription primer PLS

<400> SEQUENCE: 4
atggccagcc agtcaatc                                                    18

```
<210> SEQ ID NO 5
<211> LENGTH: 20
<212> TYPE: DNA
<213> ORGANISM: Artificial
<220> FEATURE:
<223> OTHER INFORMATION: DNA reverse transcription primer PLR

<400> SEQUENCE: 5
tcgccctaat tgaataggtg                                               20

<210> SEQ ID NO 6
<211> LENGTH: 39
<212> TYPE: DNA
<213> ORGANISM: Artificial
<220> FEATURE:
<223> OTHER INFORMATION: DNA reverse transcription primer EU-7-n-s

<400> SEQUENCE: 6
tgtaaaacga cggccagtat gataaagtcc cagcgccag                          39

<210> SEQ ID NO 7
<211> LENGTH: 40
<212> TYPE: DNA
<213> ORGANISM: Artificial
<220> FEATURE:
<223> OTHER INFORMATION: DNA reverse transcription primer EU-7-n-as

<400> SEQUENCE: 7
caggaaacag ctatgaccct gtatgagcaa ccggcagcat                         40

<210> SEQ ID NO 8
<211> LENGTH: 23
<212> TYPE: DNA
<213> ORGANISM: Artificial
<220> FEATURE:
<223> OTHER INFORMATION: DNA reverse transcription primer EU-1a-2058-s

<400> SEQUENCE: 8
tgttgaagga ttgtccgagc tcc                                           23

<210> SEQ ID NO 9
<211> LENGTH: 21
<212> TYPE: DNA
<213> ORGANISM: Artificial
<220> FEATURE:
<223> OTHER INFORMATION: DNA reverse transcription primer EU-1a-2683-as

<400> SEQUENCE: 9
agatccaaag gcgaactgct g                                             21

<210> SEQ ID NO 10
<211> LENGTH: 38
<212> TYPE: DNA
<213> ORGANISM: Artificial
<220> FEATURE:
<223> OTHER INFORMATION: DNA reverse transcription primer EU-1a-2061-s

<400> SEQUENCE: 10
tgtaaaacga cggccagttg aaggattgtc cgagctcc                           38

<210> SEQ ID NO 11
<211> LENGTH: 38
<212> TYPE: DNA
<213> ORGANISM: Artificial
```

```
<220> FEATURE:
<223> OTHER INFORMATION: DNA reverse transcription primer EU-1a-2574-as

<400> SEQUENCE: 11
tgtaaaacga cggccagttg aaggattgtc cgagctcc                                    38
```

What is claimed is:

1. A vaccine against Porcine Respiratory Reproductive Syndrome (PRRS) which comprises live PRRS virus, characterized in that it contains one or more of the PRRS virus strains that have been deposited on 27 Oct. 2004 with the European Collection of Cell Cultures (ECACC), Porton Down, Salisbury, Wiltshire, SP4 0JG, Great Britain, under the Accession Numbers ECACC 04102703, ECACC 04102702, and ECACC 04102704, or a descendant of one or more of the aforementioned strains, with a pharmaceutically acceptable carrier, but not the strain deposited under the Accession Number ECACC 04102701.

2. The vaccine of claim 1, comprising the PRRS virus strains that have been deposited under the Accession Numbers ECACC 04102703, ECACC 04102702, and ECACC 04102704.

3. The vaccine of claim 1 or claim 2, further comprising an adjuvant.

4. The vaccine of claim 3, wherein the adjuvant is (α-tocopherol acetate.

5. The vaccine of claim 1, wherein the PRRS virus is present as a freeze-dried composition of such virus.

6. A PPRS virus strain which is any one of the PRRS virus strains that have been deposited on 27 Oct. 2004 with the European Collection of Cell Cultures (ECACC), Porton Down, Salisbury, Wiltshire, SP4 0JG, Great Britain, under the Accession Numbers ECACC 04102703, ECACC 04102702, and ECACC 04102704, or a descendant of any one of the aforementioned strains.

7. A vaccine product, comprising in separate containers a freeze-dried composition according to claim 5, and a solvent for reconstitution.

8. The vaccine product as recited in claim 7 further comprising a leaflet or label with instructions for use.

9. The vaccine product of claim 7, wherein the solvent contains an adjuvant.

10. A method of vaccinating a pig against PRRS, comprising administering a vaccine or vaccine product according to claim 1 to such pig.

11. The vaccine according to claim 1, further characterised in that it comprises at least one further antigen active against a porcine disease which is not PRRS.

* * * * *